United States Patent
Berler

(10) Patent No.: US 6,626,863 B1
(45) Date of Patent: Sep. 30, 2003

(54) SAFETY SYRINGE

(75) Inventor: Barry Berler, Huntington Valley, PA (US)

(73) Assignee: NuSaf, L.L.C., Baton Rouge, LA (US)

( * ) Notice: Subject to any disclaimer, the term of this patent is extended or adjusted under 35 U.S.C. 154(b) by 231 days.

(21) Appl. No.: 09/721,350

(22) Filed: Nov. 22, 2000

(51) Int. Cl.$^7$ .............................................. A61M 5/00
(52) U.S. Cl. ........................ 604/110; 604/198; 604/263
(58) Field of Search ................................ 604/110, 192, 604/193, 198, 208, 209, 210, 220, 187, 263, 218

(56) References Cited

U.S. PATENT DOCUMENTS

| | | | |
|---|---|---|---|
| 3,094,122 A | 6/1963 | Gauthier et al. | |
| 3,368,558 A | 2/1968 | Sarnoff et al. | |
| 3,765,402 A | 10/1973 | Granhorn | |
| 4,026,287 A | 5/1977 | Haller | |
| 4,197,846 A | 4/1980 | Bucalo | |
| 4,425,120 A | 1/1984 | Sampson et al. | |
| 4,464,171 A | 8/1984 | Garwin | |
| 4,581,021 A | 4/1986 | Landau et al. | |
| 4,636,202 A | 1/1987 | Lowin et al. | |
| 4,702,738 A | 10/1987 | Spencer | |
| 4,737,150 A | 4/1988 | Baeumle et al. | |
| 4,784,157 A | 11/1988 | Halls et al. | |
| 4,826,483 A | * 5/1989 | Molnar, IV | 604/110 |
| 4,846,785 A | 7/1989 | Cassou et al. | |
| 4,846,799 A | 7/1989 | Tanaka et al. | |
| 4,850,996 A | 7/1989 | Cree | |
| 4,863,434 A | 9/1989 | Bayless | |
| 4,863,435 A | 9/1989 | Struman et al. | |
| 4,874,382 A | 10/1989 | Lindemann et al. | |
| 4,875,896 A | 10/1989 | Kurtz | |
| 4,883,471 A | 11/1989 | Braginetz et al. | |
| 4,883,472 A | 11/1989 | Michel | |
| 4,892,107 A | 1/1990 | Haber | |
| 4,894,055 A | 1/1990 | Sudnak | |
| 4,906,236 A | * 3/1990 | Alberts et al. | 604/198 |
| 4,909,791 A | 3/1990 | Norelli | |
| 4,909,792 A | 3/1990 | Norelli | |
| 4,923,445 A | 5/1990 | Ryan | |

(List continued on next page.)

FOREIGN PATENT DOCUMENTS

| | | |
|---|---|---|
| FR | 2 687 578 | 2/1992 |
| JP | 89/08468 | 9/1989 |

*Primary Examiner*—Michael J. Hayes
*Assistant Examiner*—Jennifer Maynard
(74) *Attorney, Agent, or Firm*—Roy, Kiesel, Keegan and DeNicola

(57) ABSTRACT

A safety syringe having a sheath advanceable into a covered position by operation of the plunger with a mechanism for securing the sheath in the covered position. A bar extends across the interior of the barrel. One or more arms depend from the sheath, engaging the plunger directly or indirectly. Depressing the plunger pushes the sheath, via the arms, into the covered position. The arms each include a first and a second tooth. As the sheath is advanced, the first tooth will encounter the bar. The leading edge of the first tooth is beveled to allow the tooth to pass over the bar. The trailing edge of the first tooth is not beveled, preventing the first tooth from being pulled back over the bar. The leading edge of the second tooth is likewise not beveled, also preventing the second tooth from passing over the bar. The first and second teeth lock the bar between them, preventing the sheath and arms from moving in either direction. Thus, the sheath will be locked in the covered position when the bar is between the teeth. Additional security is provided by locking the fully depressed plunger in the barrel. Locking the plunger in place will prevent the sheath from returning to the exposed position. Additionally, the fully depressed plunger is sized to be completely contained within the barrel, inhibiting access to the plunger and making forcible retraction of the plunger more difficult, thereby further inhibiting reuse of the syringe.

13 Claims, 7 Drawing Sheets

U.S. PATENT DOCUMENTS

| | | | |
|---|---|---|---|
| 4,929,237 A | | 5/1990 | Medway |
| 4,935,014 A | | 6/1990 | Haber |
| 4,935,016 A | | 6/1990 | Deleo |
| 4,936,830 A | | 6/1990 | Verlier |
| 4,944,723 A | | 7/1990 | Haber et al. |
| 4,966,592 A | | 10/1990 | Burns et al. |
| 4,966,593 A | | 10/1990 | Lennox |
| 4,969,877 A | | 11/1990 | Kornberg |
| 4,973,316 A | | 11/1990 | Dysarz |
| 4,973,317 A | | 11/1990 | Bobrove |
| 4,976,701 A | | 12/1990 | Ejlersen et al. |
| 4,982,842 A | | 1/1991 | Hollister |
| 4,986,819 A | | 1/1991 | Sobel |
| 4,994,034 A | * | 2/1991 | Botich et al. ............... 604/110 |
| 4,994,041 A | | 2/1991 | Dombrowski et al. |
| 5,015,240 A | | 5/1991 | Soproni et al. |
| 5,024,659 A | | 6/1991 | Sjostrom |
| 5,026,353 A | | 6/1991 | Bartman |
| 5,032,117 A | | 7/1991 | Motta |
| 5,049,133 A | | 9/1991 | Villen Pascual |
| 5,051,109 A | | 9/1991 | Simon |
| 5,067,942 A | | 11/1991 | Jaffe et al. |
| 5,084,034 A | | 1/1992 | Zanotti |
| 5,092,851 A | | 3/1992 | Ranger |
| 5,092,852 A | | 3/1992 | Poling |
| 5,097,842 A | | 3/1992 | Bonn |
| 5,098,401 A | | 3/1992 | De Lange |
| 5,104,384 A | | 4/1992 | Parry |
| 5,106,372 A | * | 4/1992 | Ranford ..................... 604/110 |
| 5,122,123 A | | 6/1992 | Vaillancourt |
| 5,135,507 A | | 8/1992 | Haber et al. |
| 5,151,088 A | | 9/1992 | Allison et al. |
| 5,158,549 A | * | 10/1992 | McCarthy ................... 604/110 |
| 5,188,599 A | | 2/1993 | Botich et al. |
| 5,205,825 A | | 4/1993 | Allison et al. |
| 5,205,826 A | | 4/1993 | Chen |
| 5,215,533 A | * | 6/1993 | Robb ......................... 604/195 |
| 5,256,152 A | | 10/1993 | Marks |
| 5,282,792 A | | 2/1994 | Imbert |
| 5,300,038 A | | 4/1994 | Haber et al. |
| 5,306,258 A | | 4/1994 | de la Fuente |
| 5,314,503 A | | 5/1994 | Bobrove et al. |
| 5,342,320 A | | 8/1994 | Cameron |
| 5,370,628 A | | 12/1994 | Allison et al. |
| 5,380,295 A | * | 1/1995 | Vacca ........................ 604/187 |
| 5,383,851 A | | 1/1995 | McKinnon, Jr. et al. |
| 5,385,555 A | | 1/1995 | Hausser |
| 5,407,431 A | | 4/1995 | Botich et al. |
| 5,460,611 A | * | 10/1995 | Alexander ................... 604/110 |
| 5,503,627 A | | 4/1996 | McKinnon et al. |
| 5,505,721 A | | 4/1996 | Leach et al. |
| 5,520,639 A | | 5/1996 | Peterson et al. |
| 5,540,660 A | | 7/1996 | Jenson |
| 5,665,072 A | | 9/1997 | Yoon |
| 5,720,727 A | | 2/1998 | Alexander et al. |
| 5,795,339 A | | 8/1998 | Erskine |
| 5,891,092 A | | 4/1999 | Castellano |
| 5,893,845 A | | 4/1999 | Newby et al. |
| 5,921,964 A | | 7/1999 | Martin |
| 6,110,147 A | * | 8/2000 | Perouse ...................... 604/198 |

* cited by examiner

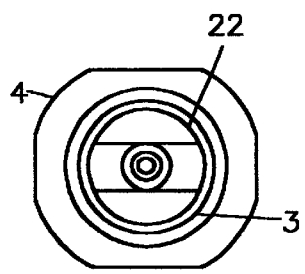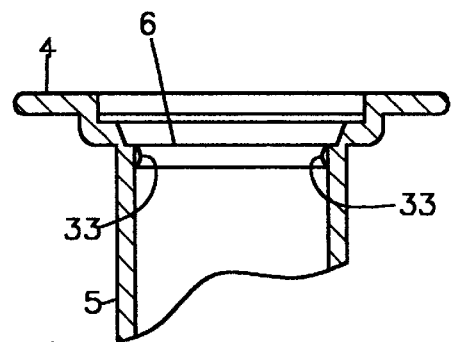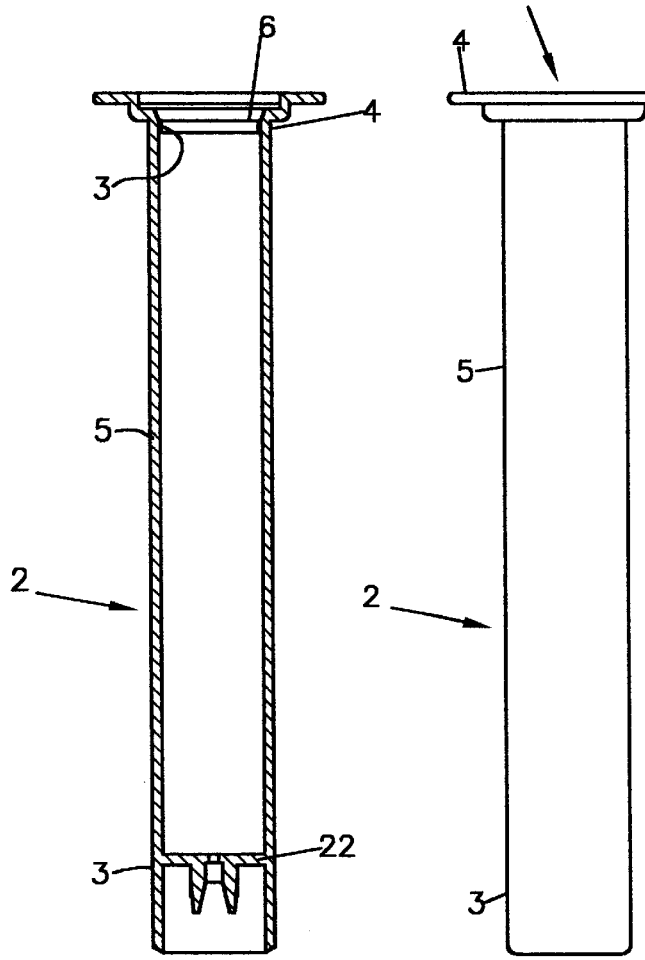

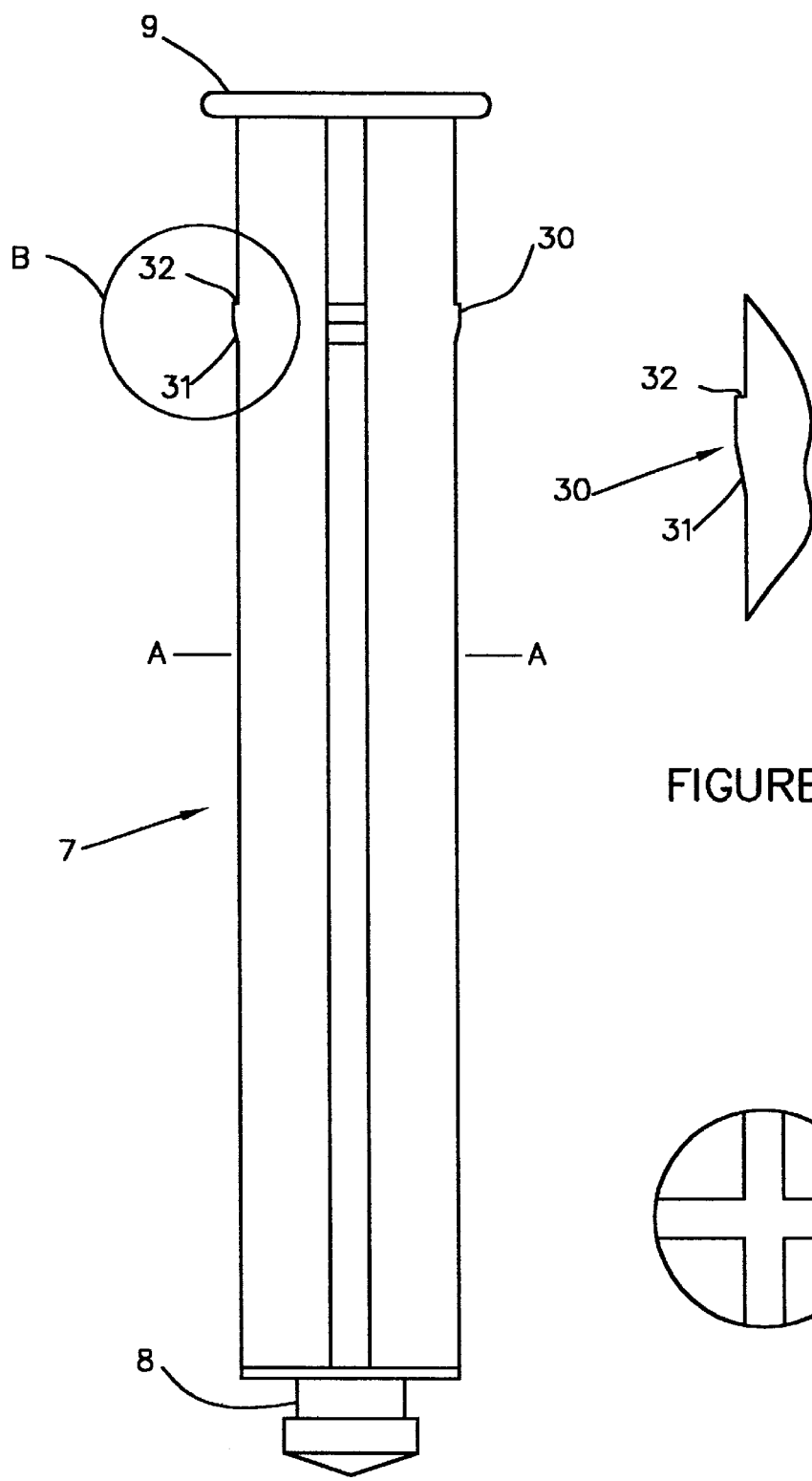
FIGURE 7
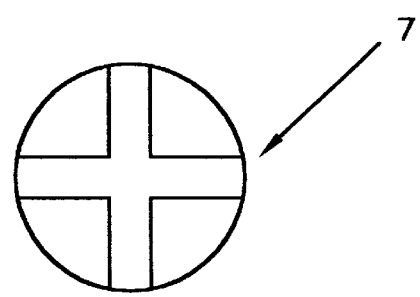
FIGURE 7B
FIGURE 7A

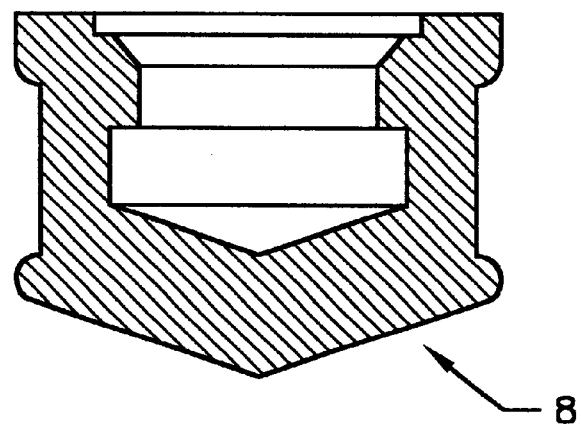
FIGURE 8
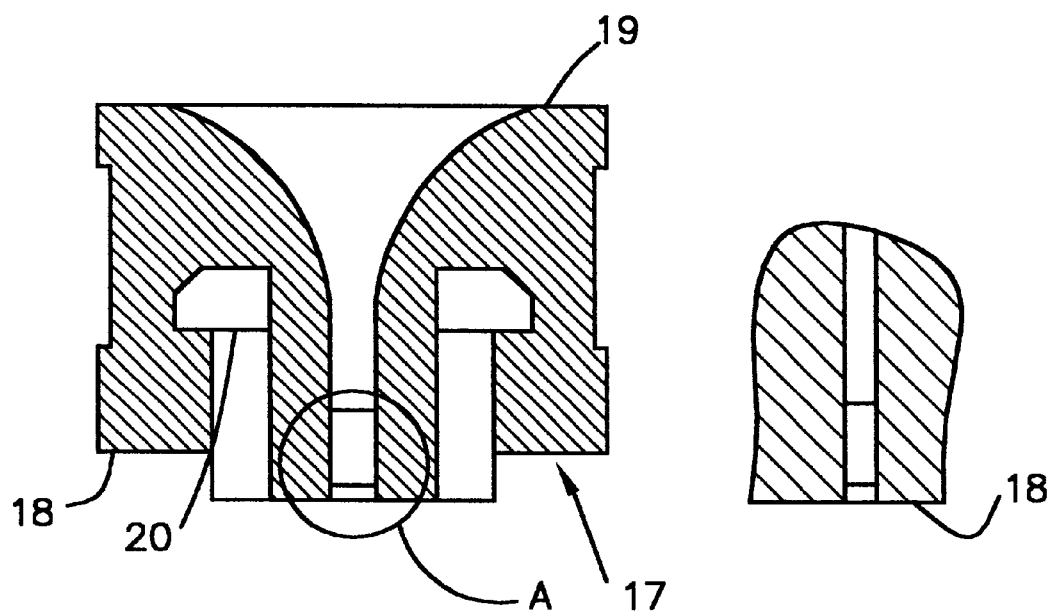
FIGURE 9
FIGURE 9A

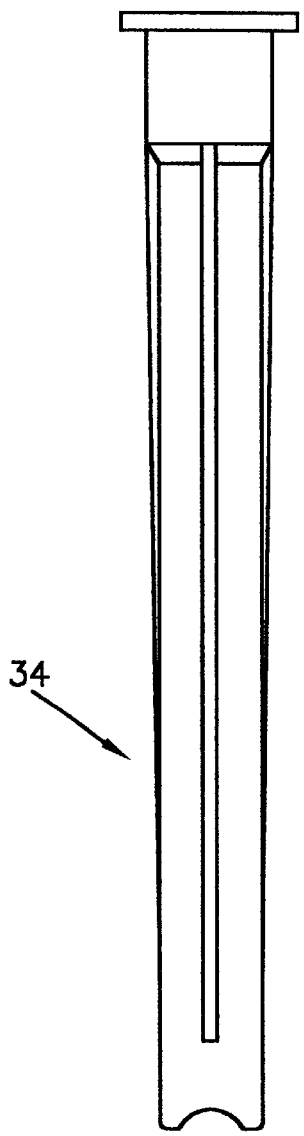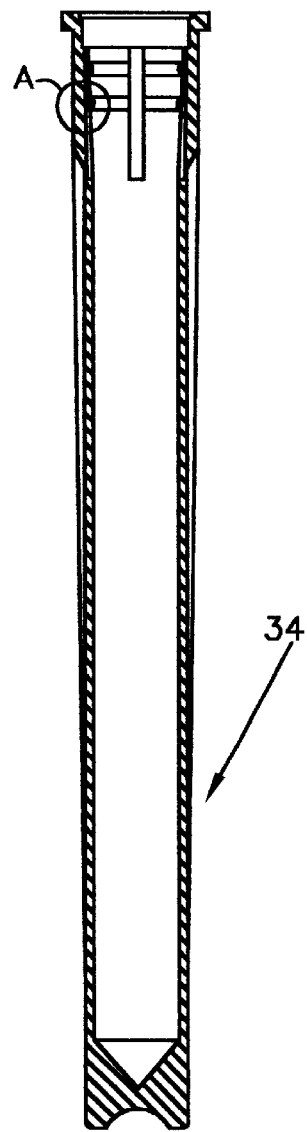
FIGURE 13    FIGURE 14
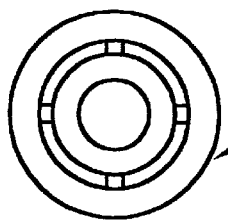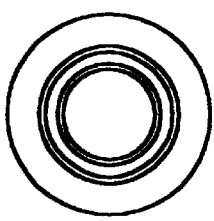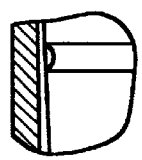
FIGURE 15    FIGURE 16    FIGURE 14A

SAFETY SYRINGE

BACKGROUND OF THE INVENTION

1. Field of the Invention

The invention relates to safety syringes in general and to an improved locking mechanism for safety syringes in particular.

2. Prior Art

In one form of safety syringe, the sheath is advanced by operation of the plunger. Examples of these safety syringes can be found in U.S. Pat. Nos. 5,720,727 and 5,460,611, which are both hereby incorporated by reference in their entirety. Syringes of this type offer excellent protection for the health care worker from accidental needle sticks; however, an additional concern is the reuse of the needles by intravenous drug users. Reuse of needles is a significant contributing factor to the spread of blood born diseases like AIDS and hepatitis. Many prior art safety syringes have locking mechanisms which are designed to secure the syringe in the safe position. However, most of these locking systems are designed to prevent the accidental return of the needle to an exposed condition. They are not designed to prevent a determined drug addict from overriding the locking mechanisms in order to reuse the needle for additional injections. While no lock or locking system can ever be completely invincible, a safety syringe meeting the following objectives is desired.

OBJECTS OF THE INVENTION

It is an object of the invention to provide a safety syringe capable of preventing accidental needle sticks.

It is another object of the invention to provide a safety syringe configured to be locked in its covered or safe position.

It is still another object of the invention to provide a safety syringe having safeguards to prevent its locking mechanism from being defeated.

It is yet another object of the invention to provide a safety syringe that cannot be used more than once.

SUMMARY OF THE INVENTION

The invention comprises a safety syringe having a barrel, a plunger slidably disposed in the barrel, and a needle extending from the needle end of the barrel. The plunger has a washer end configured to create a substantially fluid tight seal with the barrel sides. A sheath is slidably disposed over the needle. The sheath has an exposed position in which the sharp end of the needle is exposed and a covered position in which the sharp end of the needle is enclosed within the sheath. The sheath, or its tip end, is preferably hypodermically insertable. The sheath is moved from its is exposed position to its covered position by operation of the plunger. One or more arm, directly or indirectly, connects the sheath to the plunger so that when the plunger is fully depressed, the sheath will advance from the exposed position to the covered position.

There are several devices employed by the invention that lock the sheath in the covered position, either by preventing the sheath from being removed or by preventing it from being returned to the exposed position. A bar extends at least part of the way across the interior of the barrel. The arm or arms contain a pair of teeth that are designed to engage this bar. The leading edge of the first tooth is beveled to allow it to pass over the bar when the first tooth meets the bar as the arm and sheath are being advanced. The trailing edge of the first tooth is flat and will not allow the first tooth to ride back over the bar. This will prevent the sheath from backing up once the first tooth has passed the bar. The sheath, the arm, the bar, and the first tooth should be sized so that the sheath will be in the covered position by the time the first tooth passes the bar. The leading edge of the second tooth also has a flat surface. This will prevent the second tooth from passing over the bar. Thus, once the first tooth has passed the bar, the bar will be locked between the first tooth and the second tooth. While the first tooth prevents the sheath from backing up, the second tooth prevents the sheath from being removed by pulling it off over the sharp end of the needle, thus locking the sheath in the covered position.

In the preferred embodiment, there is a diaphragm that closes the needle end of the barrel. The diaphragm is preferably made of rubber and is configured to create a substantially fluid tight seal with the barrel sides. The diaphragm is provided with a central aperture which is slidably positioned around the needle so that when the plunger is fully depressed, the plunger will move the diaphragm forward along the needle. The arm or arms should be positioned so that they will be advanced by the diaphragm, and thus move the sheath into its covered position.

In a preferred embodiment, the diaphragm has a plunger side facing the plunger and a needle side facing the needle. The needle side of the diaphragm should contain one or more grooves. The plunger ends of the arms each have an enlarged head which are sized to fit into and engage the groove or grooves in the diaphragm. The enlarged heads preferably have a beveled leading edge to allow their insertion into the groove and a wide trailing edge to resist their extraction. The engagement of the arms with the diaphragm will resist extraction of the sheath over the sharp end of the needle, in combination with the second tooth's engagement with the bar.

In another preferred embodiment, the plunger and the barrel are designed to lockingly engage one another when the plunger is fully depressed, preventing the plunger from being extracted. This will secure the plunger in its fully depressed position adjacent to the diaphragm. With the plunger locked there, it will prevent the diaphragm and the sheath from being pushed back toward the plunger end of the barrel. Together with the locking engagement between the trailing edge of the first tooth and the bar, this will prevent the sheath from being pushed back into the exposed position.

The plunger is preferably sized so that the entire plunger is contained within the barrel when the plunger is fully depressed. This will make the plunger more difficult to engage when it is fully depressed, and thus more difficult to forcibly extract when it is locked in place.

BRIEF DESCRIPTION OF THE FIGURES

FIG. 4 is a cut-away side view of a preferred embodiment of the barrel.

FIG. 4A is an enlarged illustration of the circled portion A of FIG. 4.

FIG. 4B is an enlarged illustration of the circled portion B of FIG. 4.

FIG. 5 is a side view of a preferred embodiment of the barrel.

FIG. 6 is a needle end view of the a preferred embodiment of the barrel.

FIG. 7 is a side view of a preferred embodiment of the plunger.

FIG. 7A is an end view of the plunger shown in FIG. 7 cut away along line A—A.

FIG. 7B is an enlarged illustration of the circled portion B of FIG. 7.

FIG. 8 is a cut-away side view of a preferred embodiment of the washer end of the plunger.

FIG. 9 is a cut-away side view of a preferred embodiment of the diaphragm

FIG. 9A is an enlarged illustration of the circled portion A of FIG. 9.

FIG. 13 is a side view of a preferred embodiment the cover.

FIG. 14 is a cut-away side view of a preferred embodiment the cover.

FIG. 14A is an enlarged illustration of the circled portion A of FIG. 16.

FIG. 15 is a closed end view of a preferred embodiment of the cover.

FIG. 16 is an open end view of a preferred embodiment of the cover.

DETAILED DESCRIPTION OF THE PREFERRED EMBODIMENT

Figure 1:
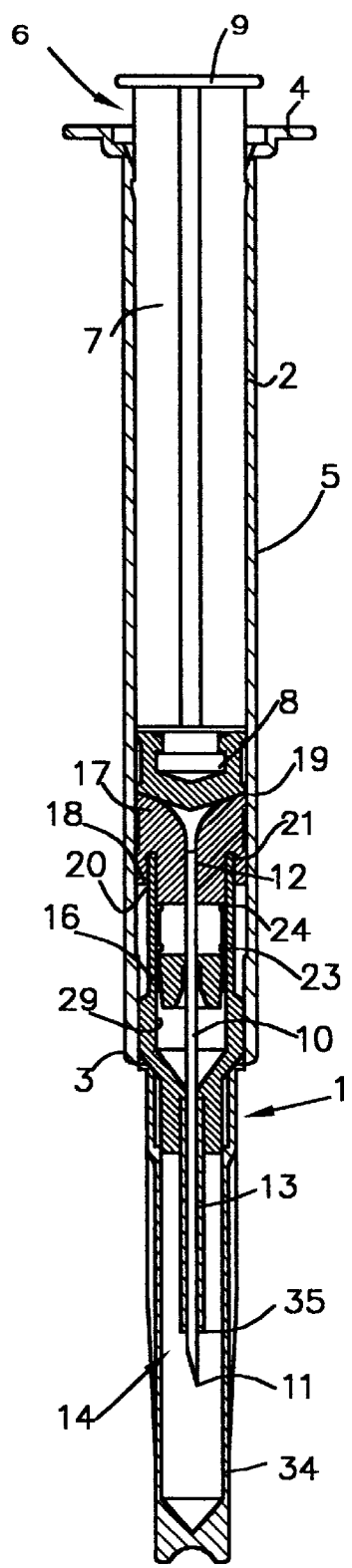
FIG. 1 is a cut-away side view of a preferred embodiment of the invention, with the plunger fully depressed but with the sheath still in the exposed position and with the cover in place over the needle.

The invention comprises a safety syringe 1 comprising a barrel 2 having a needle end 3 a plunger end 4 and sides 5 extending therebetween. Plunger end 4 contains a plunger opening 6 sized to receive a plunger 7. Plunger 7 has a washer end 8 and a control end 9, and is slidably positioned in barrel 2 so that washer end 8 is initially positioned within barrel 2 and control end 9 is positioned external to barrel 2. Washer end 8 should be configured to create a substantially fluid tight seal with barrel sides 5. Washer end 8 may be made of or covered with rubber or a rubberlike plastic and coated with an FDA approved silicone or other lubricant to help in the formation of the seal between sides 5 and washer end 8 or other rubber components of syringe 1.

Figure 2:
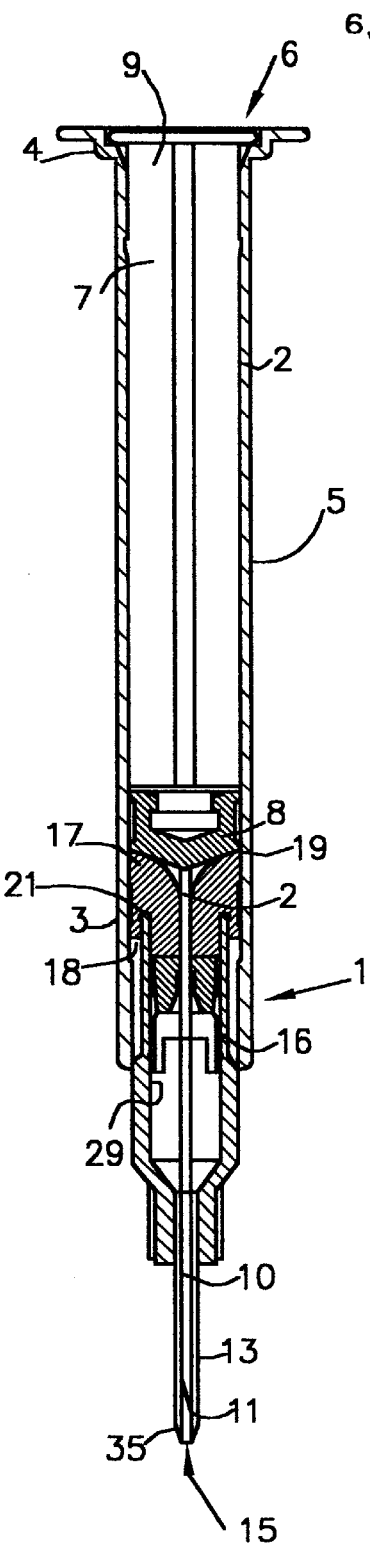
FIG. 2 is a cut-away side view of a preferred embodiment of the invention, with the plunger fully depressed and with the sheath in the covered position.
Figure 3:
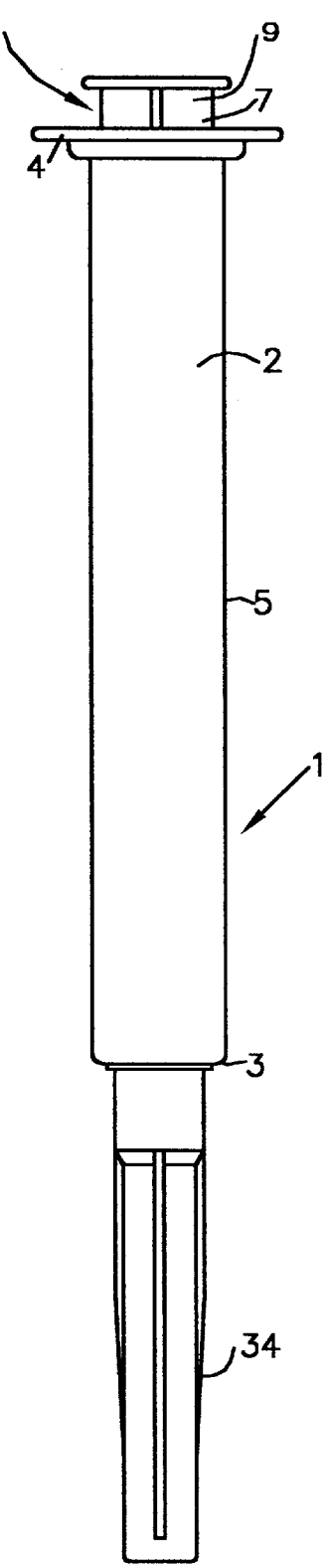
FIG. 3 is a side view of a preferred embodiment of the invention, with the cover in place over the needle.
Figure 10C:
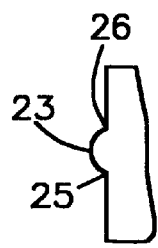
FIG. 10C is an enlarged illustration of the circled portion A of FIG. 10A.
Figure 11:
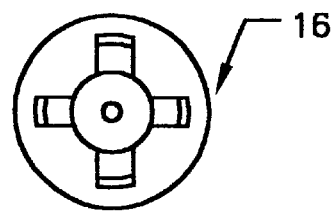
FIG. 11 is an end view of a preferred embodiment of the arms.
Figure 10A:
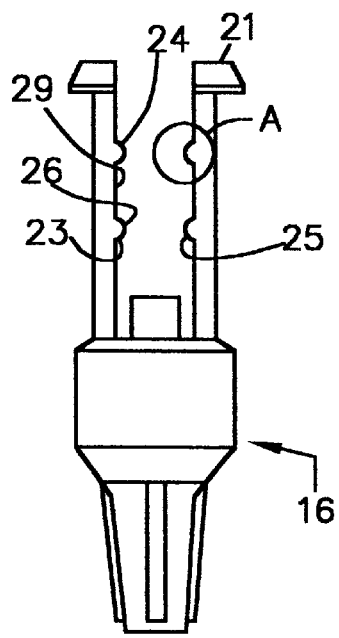
FIG. 10A is a side view of a preferred embodiment of the arms.
Figure 10B:
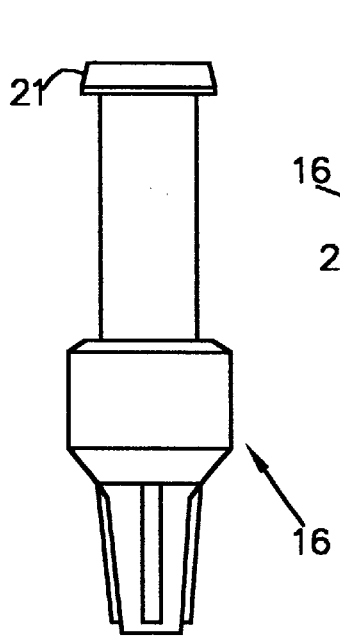
FIG. 10B is side view of the arms shown in FIG. 10A rotated 90 degrees.
Figure 10:
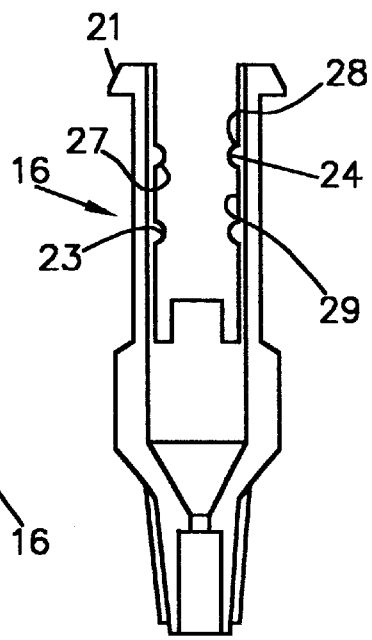
FIG. 10 is a cut-away side view of a preferred embodiment of the arms.
Figures 11A, 12:
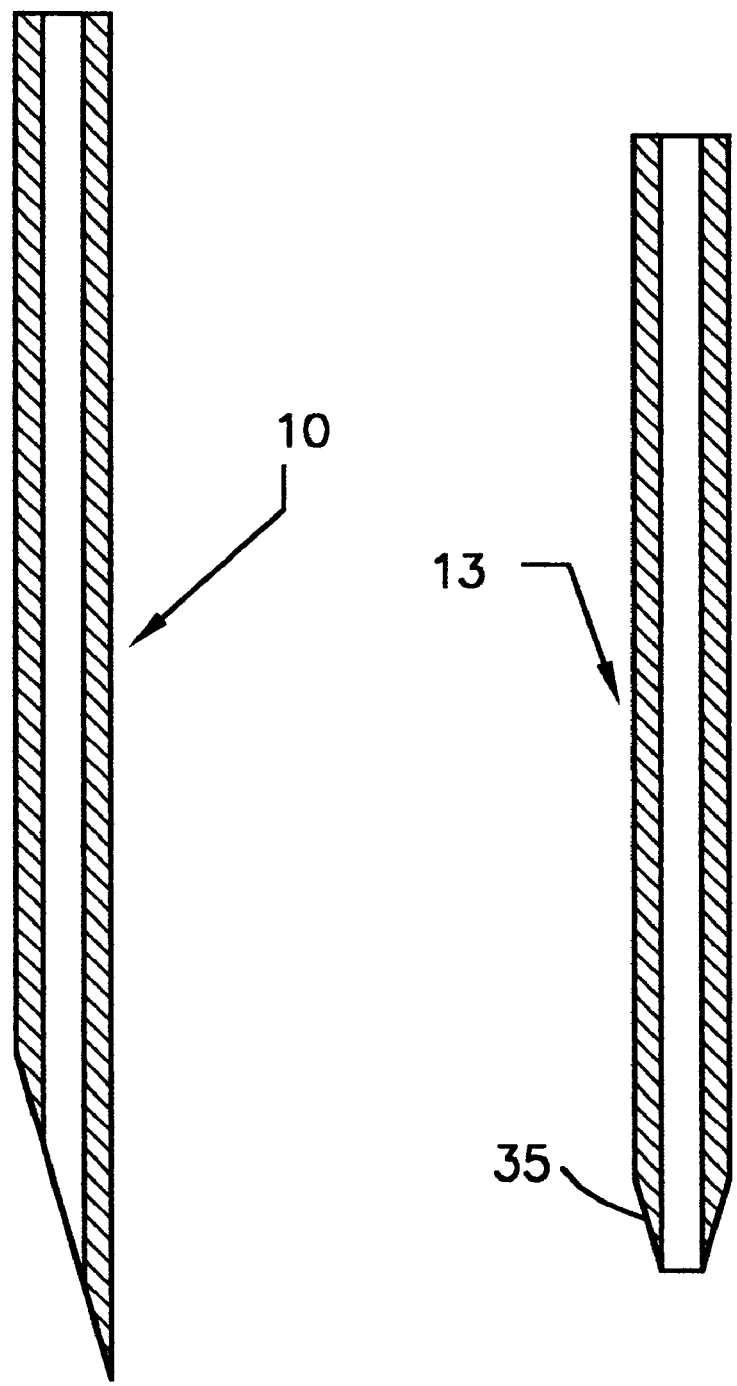
FIG. 11A is a cut-away side view of a preferred embodiment of the needle.
FIG. 12 is a cut-away side view of a preferred embodiment of the sheath.

Plunger 7 is preferably configured so that when plunger 7 is fully depressed, plunger 7 is completely contained within barrel 2, as illustrated in FIG. 2. In this position, it is preferred that control end 9 of plunger 7 be either flush with plunger end 4 of barrel 2 or between plunger end 4 and needle end 3. This will inhibit access to plunger 7 when it is fully depressed, making it more difficult to override the locking mechanism discussed below and to reuse syringe 1.

A needle 10 extends from needle end 3 of barrel 2. Needle 10 has a sharp end 11 and a barrel end 12. In the preferred embodiment, barrel end 12 is positioned inside barrel 2 and sharp end 11 is positioned external to barrel 2. Needle 10 should provide fluid passage to and from barrel 2. Needle 10 should preferably be constructed from stainless steel and is expected to typically be between about 24 to about 18 gauge, although larger or smaller needles 10 may be used when required by the particular application. In the preferred embodiment, needle 10 will have an internal diameter of between about 0.3 and about 0.6 mm and an external diameter of between about 0.56 and about 0.89 mm.

A sheath 13 is slidably positioned over needle 10. Sheath 13 is preferably made of a thin resilient material such as Ethylisoplast 2510, a DOW Product, or of TEFLON. Sheath 13 should have an exposed position 14 in which sharp end 11 of needle 10 is outside sheath 13 and a covered position 15 in which sharp end 11 is contained within sheath 13. Sheath 13 should be moveable from exposed position 14 to covered position 15 by operation of plunger 7. Preferably, this is accomplished by providing sheath 13 with one or more arms 16. Arms 16 should engage plunger 7, directly or indirectly, so that when plunger 7 is advanced it will push arms 16 and sheath 13 forward.

Syringe 1 may be provided with a diaphragm 17. Diaphragm 17 should be slidably disposed over barrel end 12 of needle 10 and configured to create a substantially fluid tight seal with barrel sides 5. Diaphragm 17 should have a needle side 18 facing the sharp end 11 of needle 10 and a plunger side 19 facing the plunger end 4 of barrel 2. In the preferred embodiment, diaphragm 17 is provided with a central needle channel 50 positioned substantially perpendicular to needle side 18 and plunger side 19. In a more preferred embodiment, needle channel 50 does not extend completely through needle side 18 of diaphragm 17. When diaphragm 17 is placed over needle 10, sharp end 11 of needle 10 will pierce needle side 18 of diaphragm 17 to reach needle channel 50. This will maximize the contact between diaphragm 17 and needle 10 and is expected to create a better seal between diaphragm 17 and needle 10 than if needle channel 50 were to extend all the way through diaphragm 17.

In the preferred embodiment, needle side 18 of diaphragm 17 should contain at least one groove 20 and arms 16 should contain an enlarged head 21. Enlarged head 21 should preferably be beveled so that its tip is larger than its rear. This will allow enlarged head 21 to be inserted into groove 20 but will resist extraction of enlarged head 21 from groove 20. Thus, groove 20 will engage arms 16 via enlarged head 21. This engagement will resist any effort to pull sheath 13 away from diaphragm 17 in the direction of sharp end 11 of needle 10. In the preferred embodiment, when plunger 7 is depressed, it will encounter diaphragm 17. Continued depression of plunger 7 will push diaphragm 17 forward along needle 10. Diaphragm 17 will already be in engagement with arms 16 or it will encounter arms 16 as it is advanced. In either case, diaphragm 17 will push arms 16, and thus sheath 13 forward as diaphragm 17 is advanced by plunger 7. Diaphragm 17, needle 10, sheath 13, arms 16, plunger 7, and barrel 2 should be appropriately sized relative to one another so that sheath 13 is in covered position 15 by the time plunger 7 is fully depressed.

Plunger side 19 of diaphragm 17 should preferably be sized to match washer end 8 of plunger 7. Preferably, plunger side 19 of diaphragm 17 has a concave conically shaped surface having an apex angle of about 140°. Washer end 8 of plunger 7 preferably has an convex conically shaped surface also of about 140°. By making washer end 8 and diaphragm 17 match, the user of syringe 1 will be able to more fully evacuate barrel 2 by depressing plunger 7, thereby reducing the risk that some of the medication contained in syringe 1 might not be administered. Making the surface of plunger side 19 of diaphragm 17 conical and concave will make plunger side 19 of diaphragm 17 act like a funnel for directing air to needle 10 when syringe 1 is pointed upward or for directing medication to needle 10 when syringe 1 is pointed downward. This will help prevent any air from being trapped in syringe 1 prior to the administration of an injection and help prevent any medication from being trapped in syringe 1 during an injection.

Syringe 1 is preferably provided with a locking mechanism for securing sheath 13 in covered position 15. One locking mechanism includes a bar 22 that extends at least partly across the interior of barrel 2. Bar 22 should preferably be substantially perpendicular to the longitudinal axis of barrel 2. Arms 16 should be provided with a first tooth 23 and preferably with a second tooth 24 as well. Arms 16 and bar 22 should be positioned so that teeth 23 and 24 will encounter bar 22 as arms 16, and sheath 13 are advanced. Teeth 23 and 24 should be positioned on arms 16 so that they face bar 22, preferably on the inside surface 29 of arms 16. First tooth 23 and second tooth 24 should be positioned relative to each other so that second tooth 24 is closer to enlarged head 21, when it is present, than first tooth 23. The space between first tooth 23 and second tooth 24 should be at least as wide as bar 22. First tooth 23 should have a leading edge 25 and a trailing edge 26. Trailing edge 26 should face enlarged head 21 and leading edge 25 should be generally opposite trailing edge 26. Second tooth 24 should have a leading edge 27 and a trailing edge 28 similarly positioned. Leading edge 25 on first tooth 23 should preferably be beveled so that first tooth 23 will deflect and pass over bar 22 when first tooth 23 encounters bar 22. Trailing edge 26 of first tooth 23 should preferably have a flat face or otherwise be configured to prevent first tooth 23 from passing back over bar 22. Leading edge 27 of second tooth 24 should also preferably be configured to prevent second tooth from passing over bar 22, preferably by providing leading edge 27 of second tooth 24 with a flat face as well. From the foregoing, it should be apparent that after first tooth 23 has passed bar 22, bar 22 will be locked between first tooth 23 and second tooth 24. This will prevent arms 16, and thus sheath 13, from being advanced or retracted from this position. By positioning and sizing arms 16, bar 22, teeth 23 and 24, needle 10 and sheath 13 appropriately relative to one another, syringe 1 can be configured so that sheath 13 is in covered position 15 by the time bar 22 is locked in place between first tooth 23 and second tooth 24. Positioning the locking mechanism within barrel 2 will shield the locking mechanism from external tampering, making the locking mechanism more difficult to defeat and thus less liable to be reused.

In one embodiment, first tooth 23 may be provided with a rounded hemispherical external shape. This will allow tooth 23 to pass over bar 22 more easily. Although such a configuration may be easier to defeat that the beveled arrangement described above, such potential deficiencies may be overcome by configuring plunger 7 to lockingly engage barrel 2 when plunger 7 is fully depressed, as described in more detail below.

It should be noted that syringe I may be used without second tooth 24. First tooth 23 will operate in the manner described above; however, second tooth 24 will not be present to prevent sheath 13 from being extracted over sharp end 11 of needle 10. This function may be performed by the interaction between enlarged head 21 and groove 20 in diaphragm 17, if present.

In another embodiment, first tooth 23 should be positioned so that it is adjacent to bar 22 prior to the advancement of arms 16. When first tooth 23 is in this position, almost any advancement of sheath 13 will cause first tooth 23 to pass over bar 22. This will minimize or eliminate any play in sheath 13 so that once it is advanced even a very slight degree, sheath 13 will be prevented from retreating toward plunger end 4 of barrel 2.

Another locking mechanism which may be used either in tandem with or instead of locking teeth 23 and 24 and bar 22 and/or enlarged head 21 and groove 20 is also contemplated. In this mechanism, plunger 7 is provided with at least one locking tooth 30. The use of multiple locking teeth 30 will create a more secure lock but may make depression of plunger 7 more difficult. While the inventor contemplates the use of two locking teeth 30 in the preferred embodiment, the number desired may vary with the application and with the size and resilience of the tooth 30.

Plunger locking tooth 30 should have a leading edge 31 facing washer end 8 of plunger 7 and trailing edge 32 facing control end 9. Sides 5 of barrel 2 contain a locking ring 33, which is preferably an annular feature, but which may simply be one or more inward indentations on sides 5 which serve to reduce the diameter of barrel 2. Plunger locking tooth 30 should be positioned on plunger 7 so that plunger locking tooth 30 will encounter locking ring 33 as plunger 7 is advanced. Leading edge 31 of plunger locking tooth 30 should be beveled so that plunger locking tooth 30 will pass over locking ring 33. Trailing edge 32 of plunger locking tooth 30 should be flat or otherwise configured to prevent plunger locking tooth 30 from passing back over locking ring 33. Plunger locking tooth 30 and locking ring 33 are preferably positioned relative to one another so that by the time plunger locking tooth 30 passes over locking ring 33, sheath 13 will be in covered position 15. Thus, the engagement between plunger locking tooth 30 and locking ring 33 will prevent plunger 7 from being withdrawn. Locked in place, plunger 7 will prevent syringe 1 from being reused and it will prevent sheath 13 from being forced back into exposed position 14. Thus, locking tooth 30 and locking ring 33 perform the same function as first tooth 23 and bar 22. As stated above, they may be used together or in place of each other. The same is true of bar 22 and second tooth 24 and enlarged head 21 and groove 20; they may be used together or is place of one another.

Plunger 7 is preferably sized so that entire plunger 7 is contained within barrel 2 when plunger 7 is fully depressed. Control end 9 of plunger 7 is preferably sized and positioned so that it is either flush with plunger end 4 of barrel 2 or between plunger end 4 and needle end 3. Locking plunger 7 in this position will make plunger 7 difficult to access which will make it more difficult to overcome the locking mechanism securing plunger 7 in its fully depressed position in barrel 2.

When syringe 1 is assembled, sheath 13 will necessarily be in exposed position 14. To protect sharp end 11 of needle 10 during shipping and preusage handling, syringe 1 is preferably provided with a removable cover 34 which encloses sharp end 11 of needle 10. When syringe 1 is ready for filling or use, cover 34 may be removed and discarded or retained and replaced over needle 10 and sheath 13 after sheath 13 has been moved into covered position 15 in order to provide additional protection. In no event should cover 34 be used instead of advancing sheath 13 into covered position 15 as this would create an opportunity for dirty needle sticks.

Sheath 13 has a tip end 35. In the preferred embodiment, at least tip end 35 of sheath 13 is hypodermically insertable with needle 10. By making sheath 13 or at least tip end 35 hypodermically insertable with needle 10, sheath 13 may be moved into covered position 15 prior to the time needle 10 is extracted from the patient by fully depressing plunger 7 before removing needle 10. If this procedure is followed, sharp end 11 of needle 10 will never be exposed after it is dirty.

In operation, the preferred embodiment of safety syringe 1 may come pre-filled or empty. In either case, the operator, typically a doctor, nurse or other health care professional, will remove cover 34 and fill syringe 1 by inserting needle 10 into a medication vial and retracting plunger 7 if syringe 1 is empty. An excess amount of medication should preferably be drawn into syringe 1. The excess may then be expelled prior to administering the injection by turning syringe 1 so that sharp end 11 of needle 10 is facing upward and depressing plunger 7 slightly. This will expel any air that may be trapped in syringe 1 and reduce the medication volume to the desired amount. At this point, sharp end 11 of needle 10 will be hypodermically inserted into the patient. If a sheath 13 that is hypodermically insertable is used, sheath 13 will be inserted with needle 10. Plunger 7 will then be depressed until all of the medication is injected into the patient. When washer end 8 of plunger 7 encounters diaphragm 17, continued pressure on plunger 7 will advance diaphragm 17 toward sharp end 11 of needle 10. Diaphragm 17 will encounter arm or arms 16, pushing them forward. As arm(s) 16 move forward, they will advance sheath 13 from exposed position 14 into covered position 15. As arms 16 move forward, they will also advance first tooth 23 and second tooth 24 into engagement with bar 22, locking sheath in covered position 15. Similarly, as plunger 7 is fully depressed, plunger locking tooth 30 will engage locking ring 33, which will prevent plunger 7 from being retracted and prevent syringe 1 from being reused. Additionally, it locking tooth 30 and locking ring 33 are ideally positioned, they will lock plunger 7 in its fully depressed position. In conjunction with or in place of teeth 23 and 24 and bar 22, this should prevent sheath 13 from being returned to exposed position 14. Finally, if plunger 7 is ideally sized, it will be completely contained within barrel 2 when it is fully depressed, preventing ready access to plunger 7 and thereby making forcible retraction of plunger 7 more difficult.

There are, of course, alternate embodiments which should be apparent to those of ordinary skill in the art in view of the foregoing description and which are intended to be included within the scope of the following claims.

I claim:

1. A safety syringe comprising a barrel having a needle end, a plunger end, and sides extending therebetween;
    a plunger slidably disposed in said barrel, said plunger having a washer end positioned closest to said needle end of said barrel, said washer end configured to create a substantially fluid tight seal with said barrel sides;
    a needle, having a sharp end and a barrel end, mounted in said barrel such that said sharp end of said needle extends beyond said needle end of said barrel;
    a sheath slidably disposed over said needle, said sheath having an exposed position wherein said sharp end of said needle is not covered by said sheath and a covered position wherein said sharp end of said needle is covered by said sheath;
    at least one arm having a sheath end facing said sheath and a plunger end facing said plunger, said arm operatively connecting said sheath and said plunger whereby said sheath may be moved from said exposed position to said covered position upon depression of said plunger; and
    a locking mechanism configured to secure said sheath in said covered position comprising:
        a bar positioned within said barrel transverse to said sides of said barrel;
        a first tooth positioned on said arm, said first tooth having a leading edge facing said sharp end of said needle and a trailing edge facing said plunger end of said barrel;
        a second tooth positioned on said arm between said first tooth and said plunger end of said arm, said second tooth having a leading edge facing said sharp end of said needle and a trailing edge facing said plunger end of said;
        said first tooth and said second tooth positioned to encounter said bar when said sheath is advanced from said exposed position to said covered position, said first tooth configured to pass over said bar when force is applied to said arm in the direction of said sharp end of said needle, said trailing edge of said first tooth configured to prevent said first tooth from passing over said bar when force is applied to said arm in the direction of said plunger end of said barrel, said second tooth configured to prevent said second tooth from passing over said bar when force is applied to said arm in the direction of said sharp end of said needle, whereby said bar may be locked between said first tooth and said second tooth; and
        wherein said needle, said sheath, said bar, said arm, said first tooth and said second tooth are configured so that said sheath is in said covered position when said bar is positioned between said teeth, whereby said sheath may be locked in said covered position by advancing said teeth until said bar is positioned between said teeth.

2. A safety syringe according to claim 1 further comprising a diaphragm slidably disposed around said barrel end of said needle, said needle configured to provide fluid passage through said diaphragm, said diaphragm configured to create a substantially fluid tight seal between said diaphragm and said barrel walls, said diaphragm positioned to engage said plunger when said plunger is depressed whereby said diaphragm may be advanced toward said sharp end of said needle, said diaphragm further positioned to engage said arm when said diaphragm is advanced toward said sharp end of said needle, whereby said sheath may be advanced by depression of said plunger.

3. A safety syringe according to claim 2 wherein said plunger end of said arm is provided with an enlarged head and wherein said diaphragm has a needle side facing said sharp end of said needle and a plunger side facing said plunger, said needle side of said diaphragm containing a groove sized to engage said enlarged head of said arm, whereby said diaphragm may provide resistance to forces exerted against said sheath in the direction of said sharp end of said needle when said groove is engaged with said head.

4. A safety syringe according to claim 3 wherein said bar is positioned to block the passage of said diaphragm toward said sharp end of said needle.

5. A safety syringe according to claim 3 further comprising at least one leg depending from said sheath, said leg positioned to encounter said bar when said sheath is in said exposed position whereby said bar and said leg will prevent said sheath from continuing to move away from said sharp end of said needle.

6. A safety syringe according to claim 2 further comprising at least one leg depending from said sheath, said leg positioned to encounter said bar when said sheath is in said exposed position whereby said bar and said leg will prevent said sheath from continuing to move away from said sharp end of said needle.

7. A safety syringe according to claim 1 further comprising at least one leg depending from said sheath, said leg positioned to encounter said bar when said sheath is in said exposed position whereby said bar and said leg will prevent said sheath from continuing to move away from said sharp end of said needle.

8. A safety syringe according to claim 1 wherein said barrel is configured to lock said plunger in place when said plunger has advanced said sheath into said covered position.

9. A safety syringe according to claim 8 wherein said barrel and said plunger are sized so that said plunger will fit completely into said barrel when said plunger is fully depressed.

10. A safety syringe according to claim 1 further comprising at least two arms.

11. A safety syringe according to claim 10 wherein each of said arms has a first tooth and a second tooth positioned to engage said bar as said sheath is advanced from said exposed position to said covered position, each said arm, said first teeth and said second teeth further configured to lock said bar between said first teeth and said second teeth when said sheath is in said covered position.

12. A safety syringe comprising a barrel having a needle end, a plunger end, and sides extending therebetween;

a plunger slidably disposed in said barrel, said plunger having a washer end positioned closest to said needle end of said barrel, said washer end configured to create a substantially fluid 1 tight seal with said barrel sides;

a needle, having a sharp end and a barrel end, mounted in said barrel such that said sharp end of said needle extends beyond said needle end of said barrel;

a sheath slidably disposed over said needle, said sheath having an exposed position wherein said sharp end of said needle is not covered by said sheath and a covered position wherein said sharp end of said needle is covered by said sheath;

at least one arm having a sheath end facing said sheath and a plunger end facing said plunger, said arm operatively connecting said sheath and said plunger whereby said sheath may be moved from said exposed position to said covered position upon depression of said plunger; and a locking mechanism configured to secure said sheath in said covered position comprising:

a locking ring positioned on the sides of said barrel facing said plunger, said locking ring creating a constriction in the diameter of said barrel;

at least one locking tooth positioned on said plunger, said plunger locking tooth configured to engage said locking ring upon advancement of said plunger, whereby the engagement of said plunger locking tooth with said locking ring will prevent the retraction of said plunger, said locking mechanism further comprising a bar positioned within said barrel transverse to said sides of said barrel; a tooth positioned on said arm, said tooth having a leading edge facing said sharp end of said needle and a trailing edge facing said plunger end of said barrel; said tooth positioned to encounter said bar when said sheath is advanced, said tooth configured to prevent said tooth from passing over said bar when force is applied to said arm in the direction of said sharp end of said needle, said tooth, said sheath, said needle, and said arm positioned so that said tooth will not engage said arm until said sheath is in said covered position.

13. A safety syringe according to claim 1, 2, 3, 4, 5, 6, 7, 8, 9, 10, 11, or 12 wherein said sheath has a tip end and wherein at least said tip end of said sheath is hypodermically insertable.

* * * * *